(12) United States Patent
Robl et al.

(10) Patent No.: US 6,235,922 B1
(45) Date of Patent: May 22, 2001

(54) PROCESSES AND INTERMEDIATES FOR PREPARING BENZO-FUSED AZEPINONE AND PIPERIDINONE COMPOUNDS USEFUL IN THE INHIBITION OF ACE AND NEP

(75) Inventors: Jeffrey A. Robl, Newton, PA (US); Chong-Qing Sun, East Windsor, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/205,316

(22) Filed: Dec. 4, 1998

Related U.S. Application Data

(62) Division of application No. 08/443,278, filed on May 17, 1995, now Pat. No. 5,877,313.

(51) Int. Cl.[7] .................................................. C07C 327/34

(52) U.S. Cl. ...................... 558/254; 548/477; 549/419; 556/426; 560/16; 560/29

(58) Field of Search ............................... 558/254; 560/16, 560/29; 548/477; 549/419; 556/426

(56) References Cited

U.S. PATENT DOCUMENTS

| | | | |
|---|---|---|---|
| 3,856,798 | 12/1974 | Meyer et al. | 260/294.8 |
| 4,105,776 | 8/1978 | Ondetti et al. | 424/274 |
| 4,186,200 | 1/1980 | Kubo et al. | 424/256 |

(List continued on next page.)

FOREIGN PATENT DOCUMENTS

| | | |
|---|---|---|
| 249223 | 12/1987 | (EP) . |
| 249224 | 12/1987 | (EP) . |
| 481522 | 4/1992 | (EP) . |
| 524553 | 1/1993 | (EP) . |
| 534363 | 3/1993 | (EP) . |
| 534396 | 3/1993 | (EP) . |
| 534492 | 3/1993 | (EP) . |
| 595610 | 5/1994 | (EP) . |
| 599444 | 6/1994 | (EP) . |
| 629627 | 12/1994 | (EP) . |
| 2207351 | 2/1989 | (GB) . |
| WO93/16103 | 8/1993 | (WO) . |
| WO94/10193 | 5/1994 | (WO) . |
| WO94/26719 | 11/1994 | (WO) . |
| WO94/28901 | 12/1994 | (WO) . |

OTHER PUBLICATIONS

Adams et al., Synthetic Communications, vol. 18, 2225–2231 (1988).
Attwood et al., FEBS Letters, vol. 165, p. 201–206 (1984).
Attwood et al., J. Chem. Perkin Trans I (1986) p. 1011–1019.
Bolos et al., J. Org. Chem., 57, 3535–3539 (1992).
Bolos et al., Tetrahedron, vol. 48, p. 9567–9576 (1992).
Boyer, T. D. "Cirrhosis of the Liver and Its Major Sequelae" in: Wyngaarden, J. B. et al., Cecil Textbook of Medicine, vol. 1 (Saunders Co., 1992) pp. 786–789.
Chackalamannil et al., Bioorganic & Medicinal Chemistry Letters, vol. 2, p. 1003–1006 (1992).
Das et al., Bioorganic & Medicinal Chemistry Letters, vol. 4, p. 2193–2198 (1994).
Delaney et al., Bioorganic & Medicinal Chemistry Letters, vol. 4, p. 1783–1788 (1994).

(List continued on next page.)

*Primary Examiner*—Richard L. Raymond
(74) *Attorney, Agent, or Firm*—Stephen B. Davis; Suzanne E. Babajko

(57) ABSTRACT

Compounds having the following formula I, and pharmaceutically acceptable salts thereof, including dual inhibitors of ACE and NEP and selective ACE inhibitors:

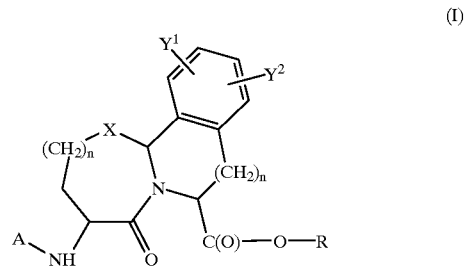

wherein:
$Y^1$ and $Y^2$ are each independently hydrogen, alkyl, aryl, halogen, or alkoxy;
X is O or $S(O)_t$;

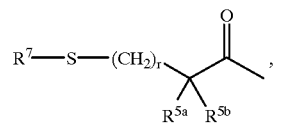

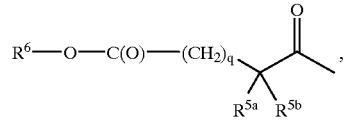

A is

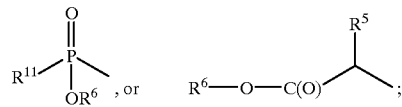

t is zero, one or two;
m and n are independently zero or one;
and wherein R, $R^5$, $R^{5a}$, $R^{5b}$, $R^6$, $R^7$, $R^{11}$, q and r are defined herein.

9 Claims, No Drawings

U.S. PATENT DOCUMENTS

| | | | |
|---|---|---|---|
| 4,192,945 | 3/1980 | Ondetti | 546/245 |
| 4,225,495 | 9/1980 | Ondetti | 260/244.4 |
| 4,337,201 | 6/1982 | Petrillo, Jr. | 548/413 |
| 4,339,600 | 7/1982 | Ondetti et al. | 562/426 |
| 4,374,829 | 2/1983 | Harris et al. | 424/177 |
| 4,409,146 | 10/1983 | Thorsett et al. | 260/239.3 |
| 4,410,520 | 10/1983 | Watthey | 424/244 |
| 4,415,496 | 11/1983 | Harris et al. | 260/239.3 |
| 4,432,971 | 2/1984 | Karanewsky et al. | 424/177 |
| 4,432,972 | 2/1984 | Karanewsky et al. | 424/177 |
| 4,460,579 | 7/1984 | Karanewsky | 424/200 |
| 4,465,679 | 8/1984 | Huang et al. | 424/244 |
| 4,470,988 | 9/1984 | Watthey | 424/263 |
| 4,473,575 | 9/1984 | Watthey | 424/263 |
| 4,477,464 | 10/1984 | Slade et al. | 424/275 |
| 4,512,924 | 4/1985 | Attwood et al. | 260/243.3 |
| 4,537,885 | 8/1985 | Watthey | 514/183 |
| 4,539,150 | 9/1985 | Katakami et al. | 260/239.3 |
| 4,548,932 | 10/1985 | Sugihara et al. | 514/211 |
| 4,575,503 | 3/1986 | Watthey | 514/213 |
| 4,584,294 | 4/1986 | Ruyle | 514/211 |
| 4,587,050 | 5/1986 | Harris et al. | 260/239.3 |
| 4,587,238 | 5/1986 | Harris et al. | 514/183 |
| 4,594,341 | 6/1986 | Cheung et al. | 514/211 |
| 4,617,301 | 10/1986 | Patchett et al. | 514/214 |
| 4,629,787 | 12/1986 | Harris et al. | 540/528 |
| 4,680,392 | 7/1987 | Harris et al. | 540/527 |
| 4,699,905 | 10/1987 | Yanagisawa et al. | 514/211 |
| 4,711,884 | 12/1987 | Karanewsky | 514/226 |
| 4,722,810 | 2/1988 | Delaney et al. | 260/402.5 |
| 4,734,410 | 3/1988 | Yanagisawa et al. | 514/212 |
| 4,749,688 | 6/1988 | Haslanger et al. | 514/19 |
| 4,801,609 | 1/1989 | Haslanger et al. | 514/506 |
| 4,824,832 | 4/1989 | Flynn et al. | 514/214 |
| 4,873,235 | 10/1989 | Parsons et al. | 514/312 |
| 4,879,309 | 11/1989 | Doll et al. | 514/513 |
| 4,963,539 | 10/1990 | Delaney | 514/119 |
| 4,973,585 | 11/1990 | Flynn et al. | 514/214 |
| 5,061,710 | 10/1991 | Haslanger et al. | 514/266 |
| 5,075,302 | 12/1991 | Neustadt | 514/211 |
| 5,098,934 | 3/1992 | Vevert et al. | 514/513 |
| 5,190,974 | 3/1993 | Clemence et al. | 514/513 |
| 5,208,236 | 5/1993 | Neustadt | 514/237.5 |
| 5,223,516 | 6/1993 | Delaney et al. | 514/339 |
| 5,225,401 | 7/1993 | Seymour | 519/19 |
| 5,232,920 | 8/1993 | Neustadt | 514/212 |
| 5,238,924 | 8/1993 | Smith | 514/19 |
| 5,262,436 | 11/1993 | Haslanger et al. | 514/513 |
| 5,362,727 | 11/1994 | Robl | 514/214 |
| 5,366,973 | 11/1994 | Flynn et al. | 514/221 |
| 5,504,080 | 4/1996 | Karanewsky | 514/214 |
| 5,508,272 | 4/1996 | Robl | 518/80 |
| 5,525,723 | 6/1996 | Robl | 540/521 |
| 5,552,937 | 9/1996 | Karanewsky et al. | 514/212 |
| 5,635,504 | 6/1997 | Ryono et al. | 514/218 |
| 5,650,408 | 7/1997 | Karanewsky et al. | 514/214 |

OTHER PUBLICATIONS

Dussaule et al., Jour. of Clinical Endocrinology and Metabolism, vol. 72, p. 653–659 (1991).

Fernandez–Cruz, The Lancet, Dec. 21/28, p. 1439–1440 (1985).

Flynn et al., J. Med. Chem., 36, p. 2420–2423 (1993).

Flynn, Tetrahedron Letters, vol. 31, p. 815–818 (1990).

Fobian et al., 206th Meeting of the Amer. Chem. Society, Aug. 1993 Abstr. ORG 297.

Fyhrquist et al., The Lancet, Dec. 21/28, p. 1439 (1985).

Hanau et al., 206th Meeting of the Amer. Chem. Society, Aug. 1993 Abstr. ORG 298.

Itoh et al., Chem. Pharm. Bull., vol. 34, p. 1128–1147 (1986).

Itoh et al., Chem. Pharm. Bull., vol. 34, pp. 2078–2089 (1986).

Laffi et al., Gastronenterology, vol. 96, p. 167–177 (1989).

Moeller et al., Tetrahedron Letters, vol. 33, p. 6041–6044 (1992).

Naming and Indexing of Chemical Substances for Chemical Abstracts, 1987 Index Guide, Section 203.

Natoff et al., Drugs Of the Future, vol. 12, p. 475–483 (1987).

Parsons et al., Biochem and Biophysical Research Comm. 117, p. 108–113 (1983).

Robl et al., Bioorganic & Medicinal Chem. Letters, vol. 4, p. 1795–1800 (1994).

Robl et al., Bioorganic & Medicinal Chemistry Letters, vol. 4, p. 1789–1794 (1994).

Robl et al., Bioorganic & Medicinal Chemistry Letters, vol. 4, p. 2055–2060 (1994).

Robl et al., J. Am. Chem. Soc., 116, p. 2348–2355 (1994).

Robl, Tetrahedron Letters, vol. 35, p. 393–396 (1994).

Robl, Tetrahedron Letters, vol. 35, p. 1393–1396 (1994).

Slade et al., J. Med. Chem., 28, p. 1517–1521 (1985).

Smith et al., Biochemistry, vol. 14, p. 766–771 (1975).

Thorsett et al., J. Med. Chem., 29, p. 251–260 (1986).

Thorsett, Actual Chim. Ther., vol. 13, p. 257–268 (1986).

Watthey et al., J. Med. Chem., 28, p 1511–1516 (1985).

Yanagisawa et al., J. Med. Chem., 30, p. 1984–1991 (1987).

Yanagisawa et al., J. Med. Chem., 31, p. 422–428 (1988).

PROCESSES AND INTERMEDIATES FOR PREPARING BENZO-FUSED AZEPINONE AND PIPERIDINONE COMPOUNDS USEFUL IN THE INHIBITION OF ACE AND NEP

This application is a division of U.S. Ser. No. 08/443,278 filed May 17, 1995 now U.S. Pat. No. 5,877,313.

FIELD OF THE INVENTION

The present invention is directed to novel benzo-fused azepinone and piperidinone compounds which are useful either as selective angiotensin converting enzyme inhibitors, or as dual inhibitors of both angiotensin converting enzyme and neutral endopeptidase. The present invention is also directed to pharmaceutical compositions containing such selective or dual action inhibitors and to methods of using such compositions, as well as to processes for preparing the novel inhibitors, novel intermediates, and processes for preparing such intermediates.

SUMMARY OF THE INVENTION

The novel compounds of this invention are benzo-fused, bicyclic oxa- or thiazepinones or piperidinones and include those compounds having the following formula I, and pharmaceutically acceptable salts thereof:

(I)

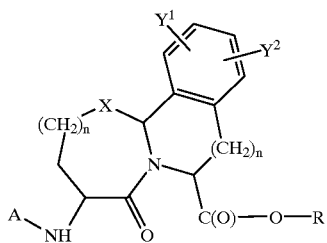

wherein:
  $Y^1$ and $Y^2$ are each independently hydrogen, alkyl, aryl, halogen, or alkoxy;
  X is O or $S(O)_t$;

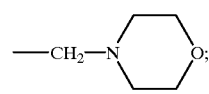

A is

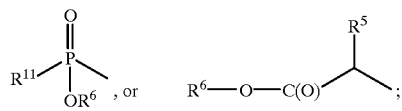

R and $R^6$ are each independently hydrogen, alkyl, substituted alkyl, aryl-$(CH_2)_p$—, substituted aryl-$(CH_2)_p$—, heteroaryl-$(CH_2)_p$—, —$CH(R^8)$—O—$C(O)$—$R^9$, or

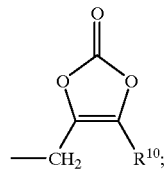

$R^5$, $R^{5a}$, and $R^{5b}$ are each independently hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene-, or $R^{5a}$ and $R^{5b}$ may form, together with the carbon to which they are bonded, a 3 to 7 membered carbocyclic ring, where said ring is optionally substituted by alkyl, or by aryl which is fused or bonded by a single bond to said ring;
$R^7$ is hydrogen, $R^8$—$C(O)$—, or $R^{12}$—S—;
$R^8$ is hydrogen, alkyl, substituted alkyl, cycloalkyl-$(CH_2)_p$—, aryl-$(CH_2)_p$—, substituted aryl-$(CH_2)_p$—, heteroaryl-$(CH_2)_p$—, or

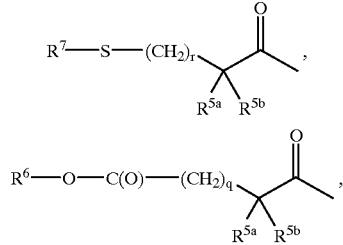

$R^9$ is hydrogen, alkyl, alkoxy, or aryl;
$R^{10}$ is alkyl, aryl-$(CH_2)_p$—, substituted aryl-$(CH_2)_p$—, or heteroaryl-$(CH_2)_p$—;
$R^{11}$ is alkyl, substituted alkyl, cycloalkyl-$(CH_2)_p$—, aryl-$(CH_2)_p$—, substituted aryl-$(CH_2)_p$—, or heteroaryl-$(CH_2)_p$—;
$R^{12}$ is hydrogen, alkyl, substituted alkyl, cycloalkyl-$(CH_2)_p$—, aryl-$(CH_2)_p$—, substituted aryl-$(CH_2)_p$—, or heteroaryl-$(CH_2)_p$—, or —S—$R^{12}$ completes a symmetrical disulfide wherein $R^{12}$ is

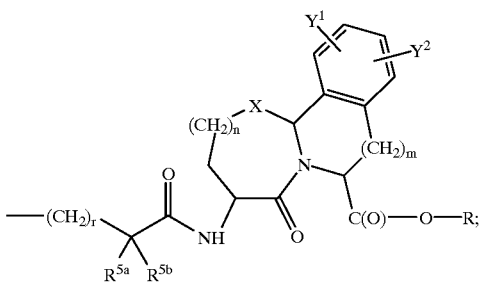

m is zero or one;
n is zero or one;
p is zero or an integer from 1 to 6;
t is zero, one or two;
q is zero or an integer from 1 to 3; and
r is zero or one.

DETAILED DESCRIPTION OF THE INVENTION

The invention is described in further detail as follows.
Definitions
The term "alkyl" refers to straight or branched chain radicals having one to seven carbon atoms, such as methyl, ethyl, n-propyl, isopropyl, tert-butyl, sec-butyl or n-butyl. The term "lower alkyl" refers to straight or branched chain radicals having one to four carbon atoms, and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)$_2$, lower alkoxy, lower alkylthio, or carboxy group.

The term "alkylene" refers to divalent straight or branched chain radicals having one to seven carbon atoms, such as —CH$_2$—, —(CH$_2$)$_2$—, $$-CH_2-\underset{CH_3}{CH}-, \quad -\underset{CH_3}{CH}-,$$

—(CH$_2$)$_3$—, —(CH$_2$)$_4$—, etc.

The terms "alkoxy" and "alkylthio" refer to such alkyl groups as defined above attached to an oxygen or sulfur, respectively.

The term "alkenyl" refers to straight or branched chain radicals of 2 to 7 carbon atoms having one or two double bonds. Preferred "alkenyl" groups are straight chain radicals of 3 to 5 carbons having one double bond.

The term "substituted alkenyl" refers to such straight or branched radicals of 2 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy group.

The term "cycloalkyl" refers to saturated rings of 3 to 7 carbon atoms with cyclopropyl, cyclobutyl, cyclopentyl, and cyclohexyl being most preferred.

The term "carbocyclic ring" refers to a ring moiety wherein all of the ring atoms are carbon atoms.

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), or —N(lower alkyl)$_2$, and di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and/or S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and/or N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl group. Also, if the mono- or bicyclic ring has an available N-atom, such N atom can also be substituted by an N-protecting group such as

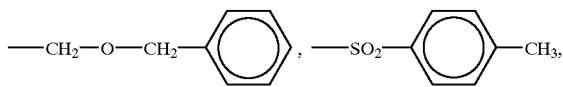

2,4-dinitrophenyl, lower alkyl, benzyl, or benzhydryl.

The terms "halogen" or "halo" refer to chlorine, bromine, fluorine and iodine.

The term "acyl", as used herein alone or as part of another group, denotes the moiety formed by the removal of the hydroxyl group from the group —COOH of an organic carboxylic acid.

The term "salt(s)" denotes acidic and/or basic salts formed with inorganic and/or organic acids and bases. Zwitterions (internal or inner salts) are included within the term "salt(s)" as used herein, as are quaternary ammonium salts such as alkylammonium salts. The nontoxic, pharmaceutically acceptable salts are preferred, although other salts may be useful, for example, in isolation or purification steps which may be employed during preparation.

Exemplary acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Exemplary basic salts include ammonium salts, alkali metal salts such as sodium, lithium, and potassium salts, alkaline earth metal salts such as calcium and magnesium salts, salts with organic bases such as amines (e.g., dicyclohexylamine, alkylamines such as t-butylamine and t-amylamine, substituted alkylamines, aryl-alkylamines such as benzylamine, dialkylamines, substituted dialkylamines such as N-methyl glucamine (especially, N-methyl-D-glucamine), trialkylamines, and substituted trialkylamines), and salts with amino acids such as arginine, lysine and so forth. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), arylalkyl halides (e.g. benzyl and phenethyl bromides), and others.

Prodrugs and solvates of the inventive compounds are also contemplated herein. The term "prodrug", as employed herein, denotes a compound which, upon administration to a subject, undergoes chemical conversion by metabolic or chemical processes to yield a compound of the formula I or a salt and/or solvate thereof. See H. Bundgaard, "Drugs of the Future", 16 (5), 443–458 (1991); and H. Bundgaard (Ed), "Design of Prodrugs" 1985 Elsevier (Amsterdam), both incorporated herein by reference. Solvates of the compounds of the formula I are preferably hydrates.

All stereoisomers of the present compounds are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

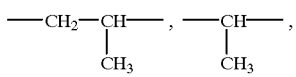

Methods for the Preparation of Compounds of the Formula I

The compounds of the formula I of the present invention may be prepared as illustrated in the following Reaction Scheme. While the following Reaction Scheme illustrates preparation of compounds of the formula I having a preferred stereochemistry, any suitable stereochemistry may be prepared by the use of the appropriate starting materials.

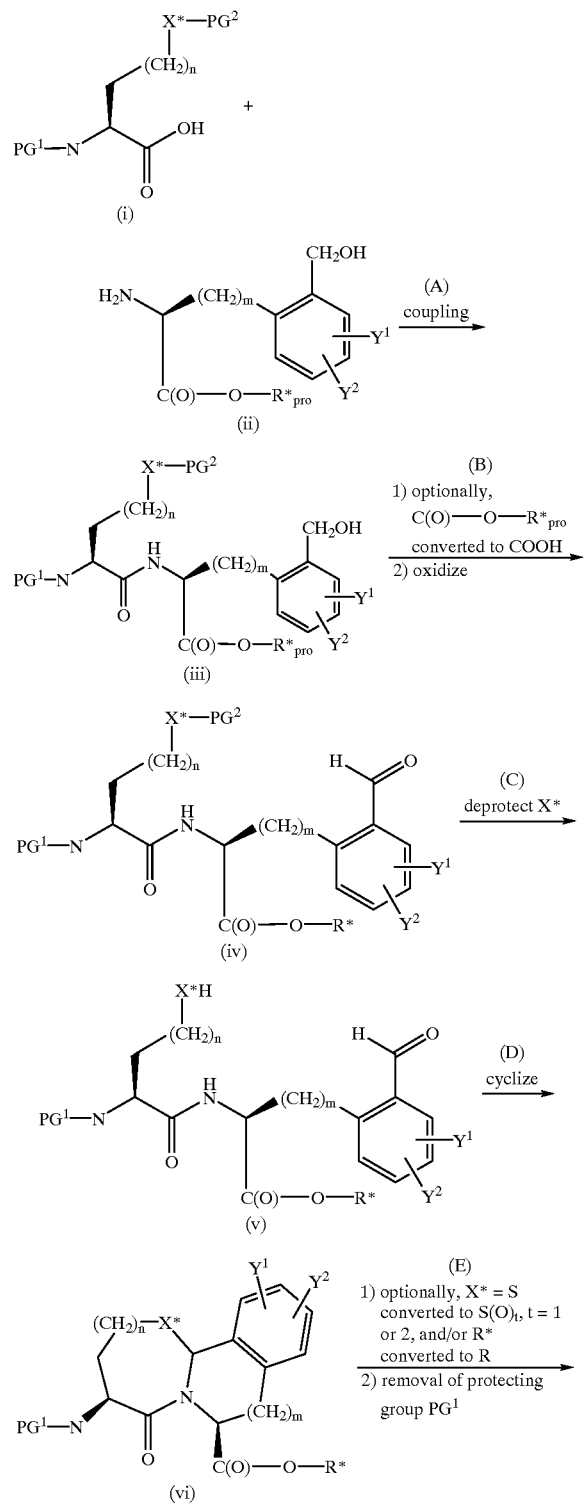

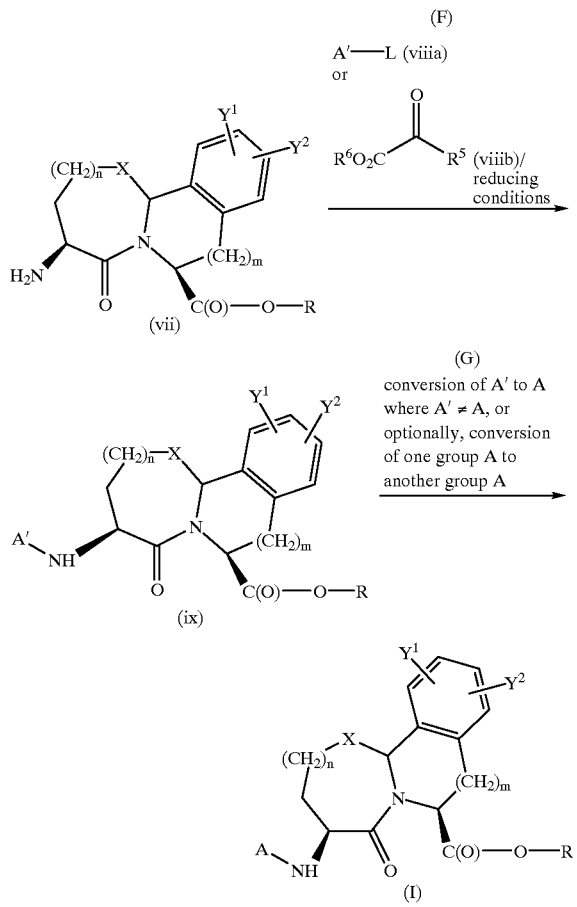

In step A of the Reaction Scheme, the starting compounds i and ii are coupled to give a dipeptide of the formula iii. This coupling reaction is preferably performed in the presence of a coupling reagent such as benzotriazol-1-yloxytris-(dimethylamino)phosphonium hexafluorophosphate (BOP reagent), a carbodiimide such as 1-ethyl-3-(3-dimethylamino)propyl carbodiimide (EDAC), or methane-sulfonyloxybenzotriazole. The starting compound of the formula i may be prepared as described in or analogous to European Patent Application 629,627, incorporated by reference herein. The starting compound of the formula ii may be prepared by methods such as those described in or analogous to Oppolzer, *Tetrahedron Letter*, 30, 6009 (1989), incorporated herein by reference, or the present Examples.

As used herein, "X*" denotes O or S, and "$PG^1$-N—" denotes a protected nitrogen atom. Exemplary groups $PG^1$-N— include those where the nitrogen is protected by a monovalent protecting group (especially, where $PG^1$-N— is benzyloxycarbonyl-NH— (i.e., Cbz-NH—) or tert-butoxycarbonyl-NH— (i.e., BOC—NH—)), or those where the nitrogen is protected by a divalent protecting group forming, together with the nitrogen, a ring (especially, where $PG^1$-N— is phthalimido). As used herein, "$PG^2$" denotes a hydroxy or mercapto protecting group. Exemplary groups $PG^2$ include acyl groups such as acetyl or benzoyl, especially acetyl, when X is sulfur, or acyl groups such as acetyl, tetrahydropyrans, trityl, or indered silyl groups such as trialkylsilyls (especially, 1,1-dimethylethyldimethylsilyl), when X is oxygen. As used herein, "$R^*_{pro}$" denotes alkyl, substituted alkyl, aryl-$(CH_2)_p$—, substituted aryl-$(CH_2)_p$—, heteroaryl-$(CH_2)_p$—, or other carboxylic acid protecting group, especially an easily removable acid protecting group not sensitive to reagents which may be employed in later reaction steps (e.g., not sensitive to the acidic reagents which may be employed in the cyclization step D), such as methyl, ethyl, t-butyl or benzyl.

In step B, the dipeptide iii is oxidized to form an aldehyde iv, for example, by treating the dipeptide iii with oxalyl chloride/dimethylsulfoxide followed by a tertiary amine in a non-protic solvent such as methylene chloride. At a point after the coupling step A and prior to the aforementioned oxidation step, or at any suitable point thereafter in this Reaction Scheme, the group C(O)—O—$R^*_{pro}$ may, optionally, be converted to a carboxylic acid group COOH. The conversion may, for example, be achieved by known methods such as by contact with an alkali metal hydroxide such as methanolic sodium hydroxide followed by contact with an aqueous acid such as HCl or $KHSO_4$ where $R^*_{pro}$ is alkyl, or by hydrogenation where $R^*_{pro}$ is benzyl. As used herein, "R*" denotes hydrogen as well as a group $R^*_{pro}$ as defined above.

The protecting group $PG^2$ of the aldehyde iv is removed in step C to yield the hydroxy or mercapto compound v. The $PG^2$ protecting group can be selectively removed from the aldehyde iv such as by treatment with a sodium alkoxide (such as sodium methoxide) in an alcohol (such as methanol) when $PG^2$ is acetyl or benzoyl; by treatment with an acid such as p-toluenesulfonic acid in an alcohol such as methanol when $PG^2$ is acetyl, benzoyl, trityl, tetrahydropyranyl, or trialkylsilyl such as 1,1- dimethylethyldimethylsilyl; or by treatment with tetra-n-butylammonium fluoride (TBAF) or hydrofluoric acid when $PG^2$ is trialkylsilyl.

In step D, the intermediate v is cyclized to form the benzo-fused bicyclic intermediate vi. Cyclization is preferably achieved by subjecting the intermediate v to an acid catalyzed cyclization reaction, most preferably by treatment with a strong acid such as trifluoroacetic acid, para-toluenesulfonic acid or a commercially available polystyrene sulfonate polymer type ion exchange resin such as Dowex AG or Amberlyst 15®. This cyclization reaction can be performed in a solvent such as methanol, methylene chloride or chloroform.

The compounds of the formula v after removal of the $PG^2$ protecting group and prior to cyclization wherein X is O can be converted to the corresponding compounds wherein X is S. This can be done by various methods. For example, the compound of formula v after removal of the $PG^2$ group can be treated with triphenylphosphine, diisopropyl azodicarboxylate and thioacetic acid. The resulting thioacetate is then treated with sodium methoxide in methanol to give the corresponding mercaptan which can then be cyclized as described above.

In another method, the compound of formula v after removal of the $PG^2$ group is treated by known methods to give a compound of the following formula x:

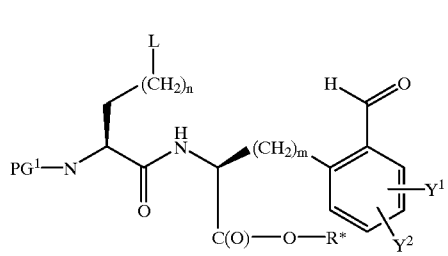

(x)

wherein L is a leaving group such as methanesulfonyloxy, para-toluenesulfonyloxy, iodo, or bromo. For example, treatment of the compound of formula v after removal of the $PG^2$ protecting group with methanesulfonyl chloride gives the compound of formula x wherein L is methanesulfonyloxy. The compound of formula x is then treated with cesium thioacetate to give the corresponding thioacetate. Treatment with sodium methoxide in methanol gives the corresponding mercaptan which can then be cyclized as described above.

In step E, the group $PG^1$-N— of the compound vi is deprotected to form a compound vii containing an amino group $H_2N$—. The method employed may, for example, be any known method suitable for the removal of the particular protecting group present, for example, treatment with hydrazine monohydrate (in a solvent such as methanol) or $CH_3(H)N$—$NH_2$ (in a solvent such as chloroform) when $PG^1$-N— is phthalimido; treatment with iodotrimethylsilane or palladium on carbon and ammonium formate or hydrogen when $PG^1$-N— is benzyloxycarbonyl-NH—; or treatment with hydrochloric acid in dioxane or other strong acid such as trimethylsilyliodide or trifluoroacetic acid when $PG^1$-N— is t-butoxycarbonyl-NH—.

At a point after the cyclization step D and prior to the aforementioned deprotection of the group $PG^1$-N—, or at any suitable point thereafter in this Reaction Scheme, $X^*$ may, when sulfur, optionally be converted to $S(O)t$ where t is one or two, and/or (i) $R^*$ may, where $R^*$ is not R, be converted to R or, (ii) where $R^*$ is a group R, $R^*$ may, optionally, be converted to a different group R.

For example, where $X^*$ is sulfur, compounds of the formula vi or compounds thereafter in the Reaction Scheme, especially compounds of the formula ix or I, may be oxidized to the corresponding compounds containing S—(O)t where t is one or two by contact with an oxidizing reagent such as metachloroperbenzoic acid, peracetic acid, monoperoxyphthalic acid, magnesium salt hexahydrate, etc. By controlling the amount of oxidizing reagent and the time of the reaction, products may be obtained wherein t is one or two.

The group —C(O)—O—$R^*$ may be converted to a group —C(O)—O—R, for example, by esterifying a carboxylic acid group previously formed at the corresponding position to yield a compound having a desired group R. An exemplary such preparation is that where a compound in which R is —$CH(R^8)$—O—$C(O)$—$R^9$ or

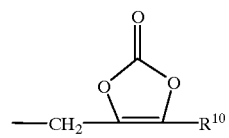

is prepared by treating the corresponding compound containing a carboxylic acid group with a compound L—$CH(R^8)$—O—$C(O)$—$R^9$ or

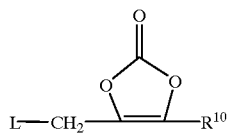

where L is a leaving group such as chloro, bromo, iodo or tolylsulfonyloxy. Groups other than the carboxylic acid group to undergo reaction may itably be protected. Preferably, conversion to a carboxylic acid group, and esterification if desired, is conducted subsequent to, or simultaneously with, step G discussed below, such as where the same reagents providing deprotection of A' also provide hydrolysis of $C(O)$—O—$R^*_{pro}$ to form a carboxylic acid group.

In step F, the amino compound vii is coupled with the compound viiia, A'—L, where L is a leaving group and A' is either a group A as described herein or a group A as described herein in which one or more groups are protected, to provide the compound ix. Preferred L groups are hydroxyl, halo (e.g., chloro), triflate (—$OSO_2CF_3$), or tolylsulfonoxy; preferred groups A' are

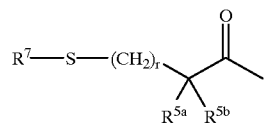

(especially, where $R^7$ is $R^8$—C(O)—, and L is hydroxyl),

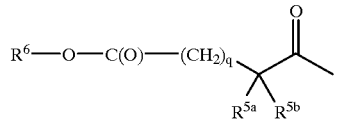

(especially, where $R^6$ is other than hydrogen, and L is hydroxyl),

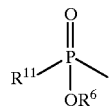

(especially, where $R^6$ is other than hydrogen, and L is halo), or

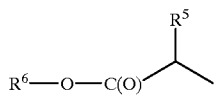

(especially, where $R^6$ is other than hydrogen, and L is triflate). Alternatively, to prepare a compound ix where A is $R^6O_2C$—$CH(R^5)$—, the amino compound vii may be contacted with a compound viiib, $R^6O_2C$—$C(O)$—$R^5$, under reducing conditions.

Step F is preferably performed in an organic solvent such as methylene chloride. The above coupling is preferably conducted in the presence of a coupling reagent, for example, 1-ethyl-3-(3-dimethylamino-propyl)carbodiimide, dicyclohexylcarbodiimide, benzotriazol-1-yloxytris(dimethylamino)phosphonium hexafluorophosphate (especially, in the presence of a tertiary amine such as triethylamine), or carbonyldiimidazole where the leaving group L is a hydroxyl group forming part of a carboxylic acid moiety. Where A'—L contains a carboxylic acid group, it can be converted to an activated form prior to coupling, such as to an acid chloride, mixed anhydride, symmetrical anhydride, activated ester, etc.

Compounds of the formula viiia may be prepared by methods described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, European Patent Application No. 629,627 etc. describing methods for the preparation of compounds of the formula

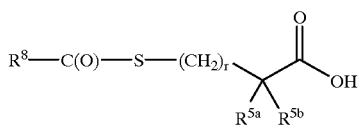

which may be used in the preparation of compounds of the formula I where A is

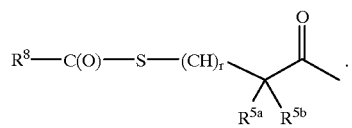

See, for example, Warshawsky et al., European Patent Application Nos. 534,396 and 534,492 describing methods for the preparation of compounds of the formula

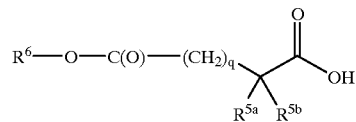

which may be used in the preparation of compounds of the formula I where A is

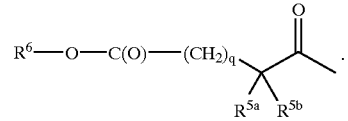

See, for example, Karanewsky et al. U.S. Pat. Nos. 4,432,971 and 4,432,972 and Karanewsky U.S. Pat. No. 4,460,579 describing methods for the preparation of phosphonochloridates of the formula

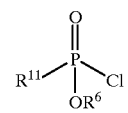

which may be used in the preparation of compounds of the formula I where A is

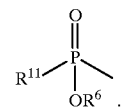

See, for example, Attwood, M. R., Hassall, C. H., Krohn, A., Lawton, G., Redshaw, S., *J. Chem. Soc. Perkin I,* p. 1011 (1986) describing methods for the preparation of compounds of the formula $R^6$—O—C(O)—CH($R^5$)-(triflate) which may be used in the preparation of compounds of the formula I where A is $R^6$—O—C(O)—CH($R^5$)—.

The keto acids and esters of the formula viiib are described in the literature. See, for example, Ruyle U.S. Pat. No. 4,584,294 and Parsons et al. U.S. Pat. No. 4,873,235.

A compound of the formula ix where A' is not a group A may be converted to a compound of the formula I in step G by removal of the protecting group(s) from A' such as by known methods. Optionally, one group A may be converted to a different group A in step G. For example:

a compound of the formula ix having a group A wherein A is

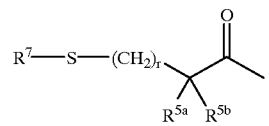

and $R^7$ is the group $R^8$—C(O)— (e.g., acetyl-S— or benzoyl-S—) may be contacted with an alkali metal hydroxide such as methanolic sodium hydroxide or with aqueous ammonium hydroxide followed by contact with an aqueous acid such as HCl or $KHSO_4$ to yield the corresponding compound where $R^7$ is hydrogen;

a compound of the formula ix where $R^7$ is hydrogen can be acylated with an acyl halide of the formula $R^8$—C (O)-halo where halo is F, Cl or Br, or acylated with an anhydride of the formula $R^8$—C(O)—O—C(O)—$R^8$, to give the corresponding compound where $R^7$ is $R^8$—C(O);

a compound of the formula ix where $R^7$ is $R^{12}$—S— and $R^{12}$ is alkyl, substituted alkyl, cycloalkyl-$(CH_2)_p$—, aryl-$(CH_2)_p$, substituted aryl-$(CH_2)_p$, or heteroaryl-$(CH_2)_p$ may be prepared by reacting the corresponding compound where $R^7$ is hydrogen with a sulfonyl compound of the formula $H_3C$—$SO_2$—S—$R^{12}$ in an aqueous alcohol solvent. The compounds of the formula $H_3C$—$SO_2$—S—$R^{12}$ are known in the literature or can be prepared by known methods (see, for example, Smith et al., Biochemistry, 14, p. 766–771 (1975));

a compound of the formula ix where $R^7$ is HS— may be prepared by reacting the corresponding compound where $R^7$ is hydrogen with $H_3C$—$SO_2$—S—C(phenyl)$_3$ or $H_3C$—$SO_2$—S—Si(alkyl)$_3$, followed by removal of the triphenylmethyl or trialkylsilyl group under acidic conditions;

symmetrical disulfides may be prepared by direct oxidation of a compound of the formula ix where $R^7$ is hydrogen with iodine according to known procedures (see, for example, Ondetti et al. U.S. Pat. No. 4,105,776);

a compound of the formula ix where A is

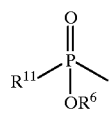

and $R^6$ is other than hydrogen may be hydrogenated to yield the corresponding compound where $R^6$ is hydrogen; and a compound where $R^6$ is —CH($R^8$)—O—C(O)—$R^9$ or

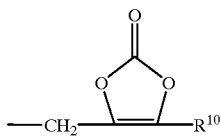

may be prepared by treating the corresponding compound where $R^6$ is hydrogen with a compound L—CH($R^8$)—O—C(O)—$R^9$ or

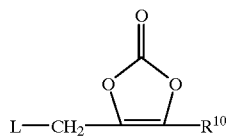

where L is a leaving group as defined above such as chloro, bromo, iodo or tolylsulfonyloxy. Groups other than the carboxylic acid group to undergo reaction may suitably be protected.

The compounds of the formula I can contain asymmetric centers. While the optically pure form of these compounds is preferred, all stereoisomeric forms are within the scope of this invention. The above described processes can utilize as starting materials, and can prepare as products, compounds in any stereoisomeric form such as optically pure compounds, racemates, enantiomers, or diastereomers. If desired, when diastereomeric compounds are prepared, they can be separated, for example, by conventional chromatographic or fractional crystallization methods; when racemates are prepared, they can be separated, for example, by conventional methods such as salt formation with an optically active reagent and separation of the diastereomers formed, or by chiral column chromatography.

Suitable salts, especially pharmaceutically acceptable salts, may be employed or prepared by the methods described herein. Preferred salts for this purpose are basic salts (especially, basic salts formed when one or both of R or $R^6$ are hydrogen), especially, alkali metal salts such as sodium and potassium, alkaline earth metal salts such as calcium and magnesium, salts derived from amino acids such as arginine, lysine, etc. and salts derived from amines such as alkylamines, e.g. t-butylamine, t-amylamine, etc., substituted alkylamines, aryl-alkylamines e.g. benzylamine, dialkylamines, substituted dialkylamines, e.g. N-methyl glucamine, trialkylamines, substituted trialkylamines, and quaternary ammonium salts. These salts can be obtained, for example, by reacting the acid form of the compound with a base supplying the desired ion in a medium such as an organic medium in which the salt precipitates, or in an aqueous medium and then lyophilizing.

Preferred Compounds

Preferred compounds of this invention are those having one or more (most preferably, all) of the following preferred substituent definitions:

$Y^1$ and $Y^2$ are hydrogen;

X is —S— or —O—;

A is

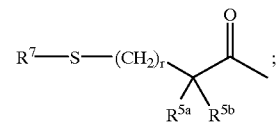

R is hydrogen or lower alkyl;

one of $R^{5a}$ and $R^{5b}$ is hydrogen and the other is alkyl, substituted alkyl, or aryl-alkylene such as benzyl;

$R^7$ is hydrogen or $R^8$—C(O)— where $R^8$ is lower alkyl;

m is one;

n is one; and r is zero or one, most preferably, those compounds having one or more (most preferably, all) of the above preferred substituent definitions and having the following stereoconfiguration:

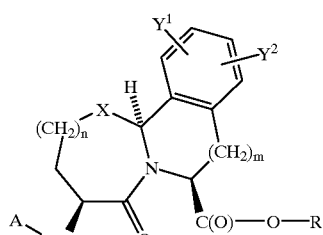

where A is

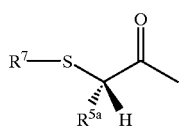

and $R^{5a}$ is alkyl, substituted alkyl or aryl-alkylene-such as benzyl.

Particularly preferred compounds are the following:

[4S-[4α(R*), 7α, 12bβ]]-4-[[2-(acetylthio)-1-oxo-3-phenylpropyl]amino]-2,3,4,5,8,12b-hexahydro-5-oxo-7H-[1,3]thiazepino[2,3-a]isoquinoline-7-carboxylic acid, methyl ester;

[4S-[4α(R*),7α, 12b]]-2,3,4,5,8,12b-hexahydro-4-[(2-mercapto-1-oxo-3-phenylpropyl)amino]-5-oxo-7H-[1,3]thiazepino[2,3-a]isoquinoline-7-carboxylic acid;

and pharmaceutically acceptable salts thereof.

Preferred Methods of Use

The compounds of the formula I where A is

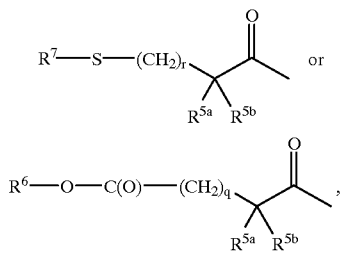

and pharmaceutically acceptable salts thereof, are dual inhibitors possessing the ability to inhibit both angiotensin converting enzyme (ACE) and neutral endopeptidase (NEP). The compounds of the formula I where A is

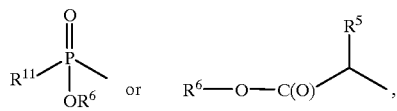

and pharmaceutically acceptable salts thereof, are selective inhibitors possessing the ability to inhibit the angiotensin converting enzyme.

The compounds of the formula I and their pharmaceutically acceptable salts are thus useful in the treatment of physiological conditions in which angiotensin converting enzyme inhibitors are useful. Such conditions include disease states characterized by abnormalities in blood pressure, intraocular pressure, and renin, including cardiovascular diseases (particularly, hypertension and congestive heart failure), glaucoma, and renal diseases (particularly, renal failure, diabetic nephropathy, and renal impairment following treatment with cyclosporine or other immunosuppressants). Other conditions in which angiotensin converting enzyme inhibitors have been reported to be useful include hepatic cirrhosis, inhibiting the progression of atherosclerosis, preventing or treating hypertensive or diabetic retinopathy, improving myocardial dysfunction during or following a myocardial infarction, and preventing restinosis after angioplasty.

The dual inhibitors are also useful in the treatment of physiological conditions in which neutral endopeptidase inhibitors are useful. Such conditions also include cardiovascular diseases (particularly hypertension), hyperaldosteronemia, renal diseases, glaucoma, as well as the relief of acute or chronic pain.

Thus, the compounds of the formula I and their pharmaceutically acceptable salts are useful, for example, in reducing blood pressure, and the dual inhibitors are further useful for this purpose due to their diuresis and natriuresis properties. The dual inhibitors are particularly useful in the treatment of congestive heart failure.

The compounds of the formula I and pharmaceutically acceptable salts thereof can be administered for the aforementioned effects, such as in amounts similar to those employed previously for other angiotensin converting enzyme inhibitors. For example, the compounds of the formula I can be administered to a mammalian host such as man at from about 1 mg to about 100 mg per kg of body weight per day, preferably from about 1 mg to about 50 mg per kg of body weight per day. The compounds of the formula I and their pharmaceutically acceptable salts are preferably administered orally, but parenteral routes such as subcutaneous, intramuscular, and intravenous routes can also be employed as can topical routes of administration. The daily dose can be administered singly or can be divided, for example, into two to four doses administered throughout the day.

The inhibitors of the formula I and their pharmaceutically acceptable salts can be administered in combination with other classes of pharmaceutically active compounds, for example, in combination with a vasoactive peptide such as ANF 99-126, a diuretic, a calcium channel blocker, a potassium channel activator, a cholesterol reducing agent, a β-blocker, an angiotensin II antagonist, etc.

The inhibitors of the formula I, their pharmaceutically acceptable salts, and other pharmaceutically acceptable ingredients, can be formulated as pharmaceutical compositions for the above described uses. Exemplary compositions for oral administration include tablets, capsules, and elixirs; exemplary compositions for parenteral administration include sterile solutions and suspensions. Exemplary compositions for treating glaucoma also include topical compositions such as solutions, ointments, and solid inserts as described in U.S. Pat. No. 4,442,089. For example, about 10 to 500 mg of active ingredient may be compounded with a physiologically acceptable vehicle, carrier, excipient, binder, preservative, stabilizer, flavoring, etc., in a unit dose form as called for by accepted pharmaceutical practice.

The following Examples are provided to illustrate the invention, and are not intended to limit the scope of the present claims. Thin layer chromatography (TLC) was performed in silica gel unless otherwise stated. Abbreviations used in the following Examples have the meaning below, unless otherwise indicated.

Abbreviations

Ac=acetyl ($CH_3$—C(O)—)
BOP reagent=benzotriazol-1-yloxytris(dimethylamino) phosphonium hexafluorophosphate
n-BuLi=n-butyllithium
CbZ=benzyloxycarbonyl
d.e.=diastereomeric excess
DMF=dimethylformamide
DMSO=dimethylsulfoxide
Et=ethyl
$Et_3N$=triethylamine
EtOAc=ethyl acetate
HMPA=hexamethylphosphoramide
HOBT=hydroxybenztriazole
m.p.=melting point Me=methyl
Me₃Al=trimethylaluminum
MeOH=methanol
NaOMe=sodium methoxide
NMM=4-methyl-morpholine
Ph=phenyl
PMA=phosphomolybdic acid
TBDMS=tert-butyldimethylsilyl
THF=tetrahydrofuran
TMSI=trimethylsilyliodide
WSC=water soluble carbodiimide (1-ethyl-3-(3-dimethylamino-propyl)carbodiimide (EDAC) used in the present Examples)

EXAMPLE 1

Preparation of [4S-[4α(R*),7α, 12bβ]]-4-[[2-(Acetylthio)-1-oxo-3-phenylproryl]amino]-2,3,4,5,8,12b-hexahydro-5-oxo-7H-[1,3]thiazepino[2,3-a] isoquinoline-7-carboxylic acid, methyl ester

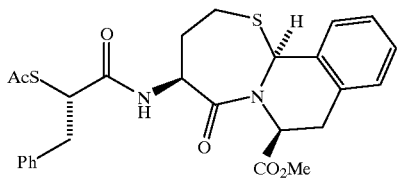

(A) 2-(Bromomethyl)benzenemethanol

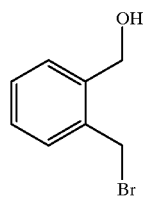

To a solution of 1M BBr₃ in CH₂Cl₂ (49.2 mL, 49.2 mmol) cooled at 0° C. was added dropwise over 45 minutes a solution of phthalan (17.40 g, 142.6 mmol) in CH₂Cl₂ (30 mL). After the addition, the mixture was heated to reflux (oil bath) for 1 hour, then cooled to room temperature and quenched with water (50 mL). The mixture was washed with H₂O (100 mL), 50% saturated NaHCO₃ (100 mL), H₂O (100 mL), brine, dried (MgSO₄) and concentrated in vacuo to give a brownish solid, which was crystallized from EtOAc/hexane to afford 16.442 g of the title compound of this step as a light yellow crystalline compound. The mother liquor was concentrated and the residue crystallized (EtOAc/hexane) to yield an additional 6.30 g of the title compound of this step (total amount of product: 22.742 g, 80% yield).

(B) 1-(Bromomethyl)-2-[[[(1,1-dimethylethyl) dimethylsilyl]oxy]methyl]benzene

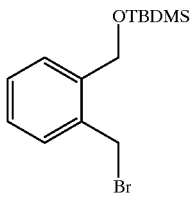

To a solution of the title compound of step (A) (10 g, 50 mmol) in CH₂Cl₂ (80 ml) cooled at 0° C. was added 2,6-lutidine (7.57 mL, 65 mmol), followed by dropwise addition of tert-butyldimethylsilyl trifluoromethane-sulfonate (14.92 mL, 65 mmol). The reaction mixture was stirred at 0° C. for 45 minutes, then quenched with H₂O (20 mL) and partitioned between EtOAc (450 mL) and H₂O (150 mL). The organic layer was separated and washed with 10% NaHCO₃ solution, brine (2×), dried (MgSO₄) and concentrated in vacuo to give a yellow syrup, which was chromatographed eluting with 10–50% EtOAc/hexane to afford 13.89 g (88%) of the title compound of this step as a light yellow oil.

(C) [3aS-(3aα, 6α, 7aβ)]1-[[[Bis-(methylthio) methylene]amino]acetyl]-hexahydro-8,8-dimethyl-3H-3a,6-methano-2,1-benzisothiazole, 2,2-dioxide

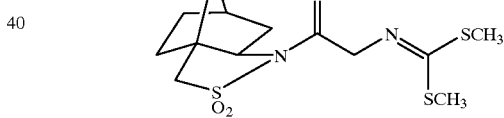

To a solution of [3aS-(3aα,6α,7aβ)]-hexahydro-8,8-dimethyl-3H-3a,6-methano-2,1-benzisothiazole, 2,2-dioxide ("D-2,10-camphor sultam", 8.40 g, 39 mmol) in toluene (210 mL) was added dropwise 2.0 M Me₃Al solution in toluene (23.4 mL, 46.8 mmol). After addition, the mixture was stirred at room temperature for 15 minutes, then a solution of N-[bis(methylthio)methylene]glycine methyl ester (10.556 g, 54.615 mmol) in 115 mL of toluene was added dropwise. After addition, the mixture was stirred at 50° C. under argon for 24 hours, then cooled down to room temperature. H₂O (13.6 mL) was added dropwise to the stirring mixture over 2 hours (with caution) to decompose the remaining Me₃Al, followed by addition of MgSO₄. After stirring for 30 minutes, the mixture was filtered and the filtrate concentrated in vacuo to give a yellow syrup, which was chromatographed using EtOAc/hexane (1:4) as a mobile phase to afford 12.787 g (87% yield) of the title compound of this step as a white solid.

(D) [3aS-[1(R*),3aα,6α,7aβ]]-1-[2-[[Bis(methylthio)methylene]amino]-3-[2-[[[(1,1-dimethylethyl)dimethylsilyl]oxy]-methyl]phenyl]-1-oxopropyl]hexahydro-8,8-dimethyl-3H-3a,6-methano-2,1-benzisothiazole, 2,2-dioxide

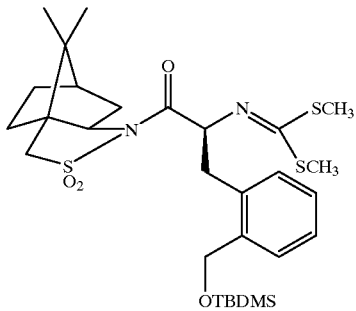

To a solution of dry THF (60 mL) cooled at −78° C. was added dropwise over 30 minutes a solution of 2.5 M n-BuLi in hexane (12.10 mL, 30.24 mmol). After addition, the title compound of step (C) (11.385 g, 30.234 mmol) in 50 mL of THF was added dropwise over 30 minutes via a dropping funnel. The resulting yellow mixture was stirred at −78° C. for 1 hour, then the title compound of step (B) (11.44 g, 36.28 mmol, 1.2 equiv.) in 15 mL of THF and 15 mL of HMPA was added over 20 minutes (the temperature of the reaction mixture was maintained at <−70° C.), followed by addition of n-tetrabutylammonium iodide (600 mg) in one portion. After addition, the temperature of the reaction mixture was warmed from −70° C. to −40° C. in one hour, and from −40° C. to 0° C. in one hour. The reaction was quenched with $H_2O$ (100 mL) at 0° C., and partitioned between EtOAc (1L) and $H_2O$ (300 mL). The organic phase was separated and washed with $H_2O$, brine, dried ($Na_2SO_4$), and concentrated in vacuo to give a yellowish syrup, which was chromatographed eluting with EtOAc/hexane (10–25%) to afford 17.40 g (95% yield) of the title compound of this step as a light yellow foam. (d.e.>99% by HPLC).

(E) [3aS-[1(R*),3aα, 6α,7aβ]]-1-[2-Amino-3-[2-(hydroxymethyl)phenyl]-1-oxopropyl]hexahydro-8,8-dimethyl-3H-3a,6-methano-2,1-benzisothiazole, 2,2-dioxide

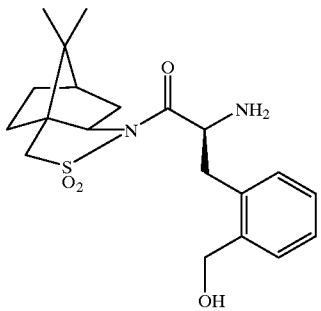

To the title compound of step (D) (6.09 g, 10 mmol) in a mixed solvent of THF (36 mL) and ethylene glycol dimethyl ether (12 mL) cooled at 0° C. was added 1 N aqueous HCl (30 mL) and $H_2O$ (15 mL). The bi-phase mixture was stirred at room temperature under argon for 24 hours. The resulting homogeneous solution was concentrated in vacuo to remove most of the THF and ethylene glycol dimethyl ether. The remaining aqueous mixture, cooled at 0° C., was adjusted to pH 7 with 10 N NaOH and extracted with EtOAc (4×120 mL). The combined EtOAc layer was washed with $H_2O$, brine, dried ($MgSO_4$) and concentrated in vacuo to give the title compound of this step as a light yellow foam which was used in the next reaction step without further purification.

(F) 2-(Hydroxymethyl)-L-phenylalanine

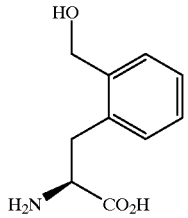

To a solution of the title compound of step (E) (ca. 10 mmol) in THF (54 mL) was added aqueous LiOH (1.69 g of LiOH monohydrate in 27 mL of $H_2O$). The mixture was stirred at room temperature under argon for 24 hours, then diluted with 50 mL of $H_2O$ and extracted with $CH_2Cl_{12}$ (4×100 mL). The aqueous phase was adjusted to pH 5.35 with 6 N HCl and concentrated in vacuo to remove most of the water. The remaining ca. 30 mL of aqueous phase was lyophilized to afford 4.01 g of light yellow solid which contained the title compound of this step and LiCl salt. The crude product was used in the next reaction step without further purification. A sample of the crude product (160 mg) in 2 mL of distilled water was loaded onto an CHP-20 column (20×150 mm) and eluted with distilled water. The ninhydrin-positive and silver nitrate-negative fractions were combined and concentrated in vacuo. The remaining aqueous solution (3–4 mL) was lyophilized to afford 67 mg of the title compound of this step as a white powder. $[\alpha]^{rT}D$ −30.5° (c 0.57, MeOH) $^1$H NMR ($D_2O$, 270 MHz): δ3.05 (dd, J=8.8, 14.6 Hz, 1H), 3.11 (dd, J=4.0, 14.6 Hz, 1H), 3.90 (m, 1H), 4.65 (s, 2H), 7.20–7.40 (m, 5H) $^{13}$C NMR ($D_2O$, 67.7 MHz): δ34.98, 57.51, 63.45, 129.87, 130.74, 131.81, 132.38, 135.96, 140.26, 175.94

Mass Spec. (FAB): $[M+H]^+$ @196, MW=195

IR (KBr): 3422, 3063, 1632, 1495, 1402, 1337, 1009, 762 $cm^{-1}$

Analysis for $C_{10}H_{13}NO_3 \cdot 0.35\ H_2O$:

Calcld: C, 59.63; H, 6.85; N, 6.95.

Found: C, 59.72; H, 6.68; N, 6.86.

(G) 2-(Hydroxymethyl)-L-phenylalanine, methyl ester, hydrochloride

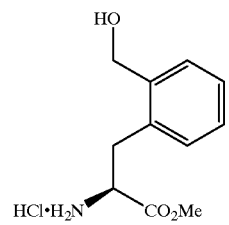

A stream of HCl gas from a lecture bottle was introduced to a suspension of the crude aminoacid title compound of step (F) (1.05 g, containing 42% of the pure aminoacid compound) in 35 mL of MeOH cooled at 0° C. until saturation. The resultant light yellow solution was stirred at room temperature for 4 hours. The volatiles were removed in vacuo, and the oily residue was azeotroped with MeOH/toluene (3×) and dried in vacuo overnight to give the title compound of this step (as a light yellow oily compound) which was used in the the next step without further purification.

(H) S-Acetyl-N-[(phenylmethoxy)carbonyl]-L-homocysteine

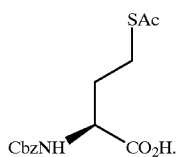

In a 1-L flask, a solution of S-[(acetyloxy)methyl]-N-[(phenylmethoxy)carbonyl]-L-homocysteine, methyl ester (prepared as described in European Patent Application 629, 627; 83.0 g, 0.233 mol) in THF (415 mL) was sparged with argon for 30 minutes. In a separate 2-L flask equipped with a mechanical stirrer and an argon inlet, a solution of 86.8% KOH (62.7 g, 0.969 mol corrected) in distilled water (280 mL) was sparged with argon for 15 minutes. The THF solution was added to the KOH solution (internal temperature 20° C.) rapidly, via cannula, with vigorous stirring under argon. The flask containing S-[(acetyloxy)methyl]-N-[(phenylmethoxy)carbonyl]-L-homocysteine, methyl ester was rinsed with 20 ml of THF (sparged with argon for 15 minutes), and the rinse was added to the reaction mixture. After 30 minutes, the reaction was clear and biphasic, and an exotherm to 28° C. had occurred. After an additional 1 hour, HPLC analysis showed complete conversion to the following intermediate:

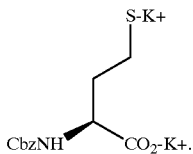

TLC silica gel (1% acetic acid in ethyl acetate) (Rf=0.51). This reaction mixture was carried forward to the next step.

After an additional 1 hour, the reaction mixture was cooled to 1° C. (internal), and NaBH$_4$ (2.75 g, 0.073 mol) was added in one portion (exotherm to 6.8° C.) to reduce the formaldehyde formed during the hydrolysis. The reaction mixture was stirred for an additional 20 minutes at 0° C. and then allowed to warm to 11° C. over 30 minutes. The reaction mixture was cooled to 1° C., and acetic anhydride (68.6 mL, 0.727 mol) was added over 10 min. An exotherm to 10° C. occurred during the addition. The internal temperature dropped back to 4° C. before the addition was complete. The cooling bath was removed, and the reaction was stirred at ambient temperature for 45 minutes. HPLC analysis showed complete conversion to the title compound of this step.

The reaction mixture was concentrated in vacuo to approximately half of its volume, acidified to pH 2 with 6N HCl (175 mL), and extracted with ethyl acetate (2×1.1 L). The combined organic extracts were washed with brine (560 mL). The organic layer was treated with activated carbon and anhydrous MgSO$_4$, filtered, and concentrated in vacuo to a yellow oil with a homogeneity index of 90.8 and HPLC enantiomeric purity of 99.30%. n-Butyl acetate ("n-BuOAc", 380 mL) was added, and the solution was concentrated in vacuo (45° C.) to half of its volume. Concentration of the crude product from n-butyl acetate removed residual acetic acid. A second portion of n-butyl acetate (180 mL) was added and concentrated again such that 190 mL of n-butyl acetate remained (2.5 mL of n-BuOAc/g of theoretical output). Heptane (300 mL) was added slowly with stirring to haziness, and seed crystals were added. After 15 minutes a white solid crystallized from the solution. A second portion of heptane (510 mL) was added slowly over 30 minutes, and the resulting slurry was stirred at room temperature overnight. The product was collected by filtration, washed with 1:3 n-BuOAc:heptane (2×275 mL) and hexane (2×275 mL), air-dried, and then dried under high vacuum to produce the title compound of this step as a white solid (50.1 g, 69%) with an HPLC enantiomeric purity of 99.84%. The filtrate was concentrated so that 100 mL of BuOAc remained. This solution was treated with 310 mL of heptane as described above to obtain a second crop as a white solid (8.4 g, 11%, enantiomeric purity: 99.78%). m.p. 73–74° C.

(I) N-[S-Acetyl-N-[(phenylmethoxy)carbonyl]-L-homocysteinyl]-2-(hydroxymethyl)-L-phenylalanine, methyl ester

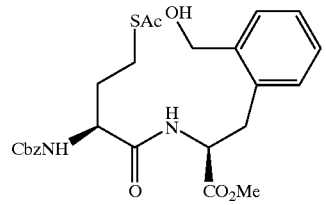

To a suspension of the title compound of step (H) (0.93 g, 2.99 mmol) and HOBt (0.444 g, 3.29 mmol) in 8 mL of CH$_2$Cl$_2$ cooled at 0° C. was added WSC (0.601 g, 3.136 mmol) in one portion. The mixture was stirred at 0° C. for 40 minutes, then the title compound of step (G) in DMF (7 mL) was added, followed by NMM (0.65 mL, 5.97 mmol). The mixture was stirred at 0° C. for 1 hour, then at room temperature for 1.5 hours. The reaction mixture was diluted with EtOAc (150 mL), washed with 5% KHSO$_4$ (2×), sat. NaHCO$_3$ (2×), H$_2$O (1×), brine, dried (MgSO$_4$), filtered and concentrated in vacuo. The residue was chromatographed eluting with 50% EtOAc/hexane to give 964 mg of partially purified product, and chromatographed again eluting with 30%–50% EtOAc/hexane to give as pure the title compound of this step (R$_f$ 0.21, 1:1 EtOAc/hexane) (790 mg, 68%) as a white foam.

(J) N-[S-Acetyl-N-[(phenylmethoxy)carbonyl]-L-homocysteinyl]-2-formyl-L-phenylalanine, methyl ester

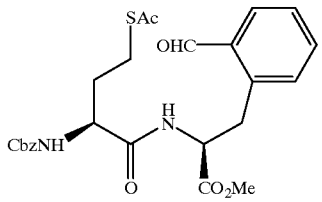

To a solution of oxalyl chloride (192 μL, 2.2 mmol) in CH$_2$Cl$_2$ (3 mL) cooled at −78° C. was added DMSO (312 μL, 4.4 mmol). After stirring at −78° C. for 5 minutes, a solution of the title compound of step (I) (790 mg, 1.572 mmol) in CH$_2$Cl$_2$ (9 mL) was added dropwise. The resultant white suspension was stirred at −78° C. for 30 minutes, before Et$_3$N (0.964 mL, 6.916 mmol) was added. The reaction mixture was warmed up at −30° C. and stirred for 1 hour. The mixture was diluted with EtOAc (100 mL), washed with 5% KHSO$_4$ (2×), sat. NaHCO$_3$ (1×), H$_2$O (2×), brine, dried (MgSO$_4$), filtered and concentrated in vacuo to give 0.77 g (98%) of the title compound of this step as a white foam.

(K) 2-Formyl-N-[N-[(phenylmethoxy)carbonyl]-L-homocysteinyl]-L-phenylalanine, methyl ester

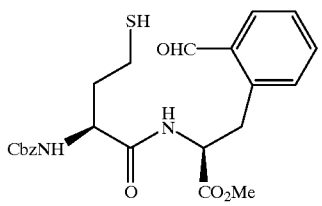

A solution of the title compound of step (J) (0.77 g, 1.54 mmol) in MeOH (16 mL) and CH$_2$Cl$_2$ (3 mL) cooled at 0° C. was purged with argon for 20 minutes. To this solution 370 μL of NaOMe (25% w/w in MeOH) was added dropwise. After addition, the mixture was stirred at 0° C. for 15 minutes before being quenched with sat. aqueous NH$_4$Cl (20 mL). The mixture was extracted with EtOAc (200 mL). The separated aqueous phase was back-extracted with EtOAc (50 mL). The combined EtOAc was washed with sat. aqueous NH$_4$Cl, H$_2$O, brine, dried (MgSO$_4$), filtered, concentrated and dried in vacuo to give 0.736 g of the title compound of this step as a white foam which was used in the next reaction step without further purification.

(L) [4S-(4α,7α,12bβ)]-2,3,4,5,8,12b-Hexahydro-5-oxo-4-[[(phenylmethoxy)carbonyl]amino]-7H-[1,3]thiazepino[2,3-a]isoquinoline-7-carboxylic acid, methyl ester

To a solution of the title compound of step (K) (0.73 g, 1.54 mmol) in CH$_2$Cl$_2$ (25 mL) was added trifluoroacetic acid (120 μL) and the reaction mixture was refluxed (60° C. oil bath) for 1.5 hours. After the mixture was allowed to cool down to room temperature, the volatiles were removed in vacuo. The residue was dissolved in EtOAc (100 mL), washed with sat. NaHCO$_3$, H$_2$O, brine, dried (MgSO$_4$), filtered and concentrated in vacuo to give 0.68 g of crude product which was chromatographed eluting with 20–25% EtOAc/hexane to give 555 mg (81.8% over 2 steps) as pure the title compound of this step (white foaming compound).

(M) [4S-(4α,7α,12bβ)]-4-Amino-2,3,4,5,8,12b-hexahydro-5-oxo-7H-[1,3]thiazepino[2,3-a]isoquinoline-7-carboxylic acid, methyl ester

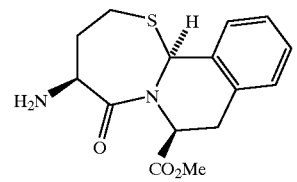

To a solution of the title compound of step (L) (545 mg, 1.237 mmol) in CH$_2$Cl$_2$ (5 mL) was added TMSI (230 μL, 1.61 mmol). The resultant dark-brown solution was stirred at room temperature under argon for 1 hour. TLC indicated the reaction was not complete; additional TMSI (100 μL, 0.7 mmol) was added. The reaction mixture was stirred for another hour before being concentrated in vacuo. The residue was taken into EtOAc (100 mL), and extracted with 0.2N HCl (4×10 mL). The combined acidic aqueous layer was extracted with EtOAc, cooled at 0° C., basified with 4N NaOH to pH=10–11 and extracted with CH$_2$Cl$_2$ (4×50 mL). The combined CH$_2$Cl$_2$ layer was washed with brine, dried (Na$_2$SO$_4$), filtered and concentrated in vacuo to give 120 mg of crude product, which was chromatographed eluting with 3–5% MeOH/CH$_2$Cl$_2$ to give 59 mg (15%) as pure the title compound of this step (an oily compound).

(N) [4S-[4α(R*),7α,12bβ]]-4-[[2-(Acetylthio)-1-oxo-3-phenylpropyl]amino]-2,3,4,5,8,12b-hexahydro-5-oxo-7H-[1,3]thiazepino[2,3-a]isoquinoline-7-carboxylic acid, methyl ester To a solution of (S)-α-(acetylthio)benzene-propanoic acid (prepared as described in European Patent Application 629, 627; 52 mg, 0.231 mmol) in CH$_2$Cl$_2$ (0.5 mL) cooled at 0° C. was added Et$_3$N (28 μL, 0.202 mmol), followed by addition of the title compound of step (M) (59 mg, 0.193 mmol) in CH$_2$Cl$_2$ (1.0 mL), then BOP reagent (102 mg, 0.231 mmol). The mixture was stirred at 0° C. for 1 hour, then at room temperature for 2 hours. The reaction mixture was diluted with EtOAc (50 mL), washed with 5% KHSO$_4$, saturated NaHCO$_3$, H$_2$O, brine, and dried (MgSO$_4$). The filtrate was evaporated to dryness and the residue flash chromatographed eluting 30% EtOAc/hexane to give 83.2 mg (84%) of the title compound of this Example as a white foam.

TLC: R$_f$=0.46 (1:1 EtOAc/hexane) (UV and PMA detection)

$^1$H NMR (CDCl$_3$, 400 MHz): δ1.98 (m, 1H), 2.34 (s, 3H), 2.38 (m, 1H), 2.97–3.10 (m, 3H), 3.27–3.47 (m, 3H), 3.73 (s, 3H), 4.29 (t, J=7.5 Hz, 1H), 5.03 (m, 2H), 6.28 (s, 1H), 7.18–7.27 (m, 8H), 7.37–7.41 (m, 2H).

EXAMPLE 2

Preparation of [4S-[4α(R*),7α,12bβ]]-2,3,4,5,8,12b-Hexahydro-4-[(2-mercapto-1-oxo-3-phenylpropyl)amino]-5-oxo-7H-[1,3]thiazepino[2,3-a]isoquinoline-7-carboxylic acid

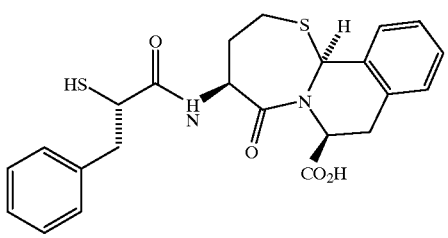

A solution of the title compound of Example 1 (83 mg, 0.162 mmol) in MeOH (1 mL) cooled at 0° C. was purged with argon for 20 minutes, then treated dropwise with a previously purged 1 M NaOH solution (1 mL, 6.0 equiv). The reaction was stirred at 0° C. for 2 hours, then at room temperature for 1.5 hours, while maintaining the bubbling of argon. TLC indicated the reaction was not complete. A few crystals of LiOH were added and the reaction mixture stirred for an additional 0.5 hour, then acidified with 5% KHSO$_4$ to pH 1–2 and extracted with EtOAc (3×). The combined EtOAc was washed with H$_2$O, brine, dried (MgSO$_4$), filtered and concentrated in vacuo to dryness. The residue was flash chromatographed using 1.25% AcOH in EtOAc as a mobile phase to afford 60 mg (81%) as an off-white foam. The compound was dissolved in aqueous acetonitrile (with drops of EtOAc and MeOH added in to aid in solubilizing the compound) and lyophilized to give the final form of the title compound of this Example as off-white powder.

Rf=0.84, 5% AcOH/EtOAc (UV and PMA detection) [α]$^{rt}$D=−72.5° (c 0.2, EtOAc) (rt=room temperature).

$^1$H NMR (CD$_3$OH+drop of CDCl$_3$, 400 MHz): δ2.14 (m, 1H), 2.33 (m, 1H), 2.98 (dd, J=7.5, 14.0 Hz, 1H), 3.08 (dd, J=4.0, 14.0 1H), 3.24 (m, 2H), 3.35 (m, 2H), 3.72 (t, J=5.0 Hz, 1H), 4.64 (dd, J=5.0, 9.0 Hz, 1H), 5.14 (m, 1H), 6.52 (s, 1H), 7.13–7.30 (m, 8H), 7.41 (m, 1H) (the protons of HS, NH and COOH are not seen due to CD$_3$OD as co-solvent).

$^{13}$C NMR (CD$_3$OH+drop of CDCl$_3$, 100 MHz): δ31.26, 31.73, 33.42, 42.40, 44.43, 52.62, 56.73, 61.40, 127.62, 127.99, 128.38, 128.76, 129.23, 129.40, 130.15, 134.20, 134.29, 139.15, 173.13, 173.90, 172.63, 175.05.

Mass Spec. [M+H]$^+$ @457, MW=456.

IR (KBr): 3345, 3028, 2924, 2556, 1732, 1643, 1497, 1437, 1422, 1186, 737, 700 cm$^{-1}$.

Analysis for C$_{23}$H$_{24}$N$_2$O$_4$S$_2$. 0.86 H$_2$O:

Calc'd: C, 58.53; H, 5.49; N, 5.93; S, 13.58.

Found: C, 58.74; H, 5.30; N, 5.72; S, 13.59.

EXAMPLE 3

1000 tablets each containing the following ingredients:

| | |
|---|---|
| Compound of Example 1 | 100 mg |
| Cornstarch | 100 mg |
| Gelatin | 20 mg |
| Avicel (microcrystalline cellulose) | 50 mg |
| Magnesium stearate | 5 mg |
| | 275 mg | are prepared from sufficient bulk quantities by mixing the title product of Example 1 and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 100 mg of active ingredient.

In a similar manner, tablets containing 100 mg of the title product of Example 2 can be prepared.

Similar procedures can be employed to form tablets or capsules containing from 10 mg to 500 mg of active ingredient.

What is claimed is:

1. A method for preparing a compound having the following formula iii:

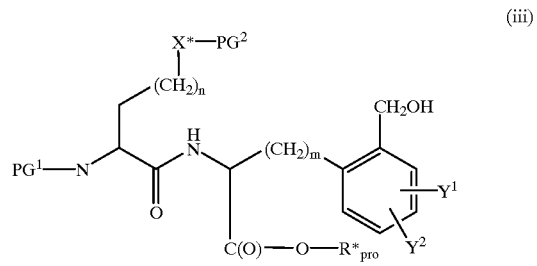

(iii)

where

Y$^1$ and Y$^2$ are each independently hydrogen, alkyl, aryl, halogen, or alkoxy;

R*$_{pro}$ denotes alkyl, substituted alkyl, aryl-(CH$_2$)$_p$—, substituted aryl-(CH$_2$)$_p$—, heteroaryl-(CH$_2$)$_p$—, or other carboxylic acid protecting group;

X* is O or S;

PG$^1$-N— denotes a protected nitrogen atom;

PG$^2$ denotes a hydroxy or mercapto protecting group;

m is zero or one;

n is zero or one; and p is zero or an integer from 1 to 6;

comprising the step of coupling the following compounds i and ii:

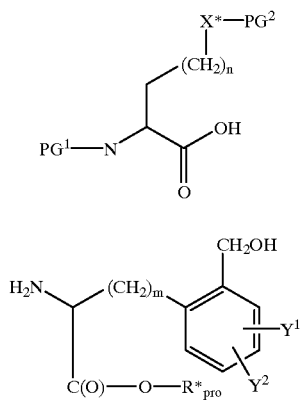

(i)

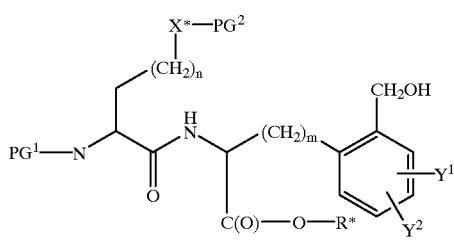

(ii)

and, optionally, hydrolyzing said group C(O)—O—R*$_{pro}$ of said compound of the formula iii to form a carboxylic acid group COOH.

2. A compound having the following formula iii, and salts thereof:

(iii)

where

Y$^1$ and Y$^2$ are each independently hydrogen, alkyl, aryl, halogen, or alkoxy;

R* denotes hydrogen, alkyl, substituted alkyl, aryl-(CH$_2$)$_p$—, substituted aryl-(CH$_2$)$_p$—, heteroaryl-(CH$_2$)$_p$—, or other carboxylic acid protecting group;

X* is O or S;

PG$^1$-N— denotes a protected nitrogen atom;

PG$^2$ denotes a hydroxy or mercapto protecting group;

m is zero or one;

n is zero or one; and p is zero or an integer from 1 to 6.

3. A compound of claim 2, wherein said compound is N-[S-acetyl-N-[(phenylmethoxy)carbonyl]-L-homocysteinyl]-2-(hydroxymethyl)-L-phenylalanine, methyl ester having the structure:

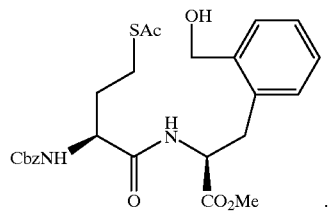

4. The method of claim 1, wherein, further, said compound of the formula iii or hydrolyzed derivative thereof is oxidized to form a compound of the following formula iv:

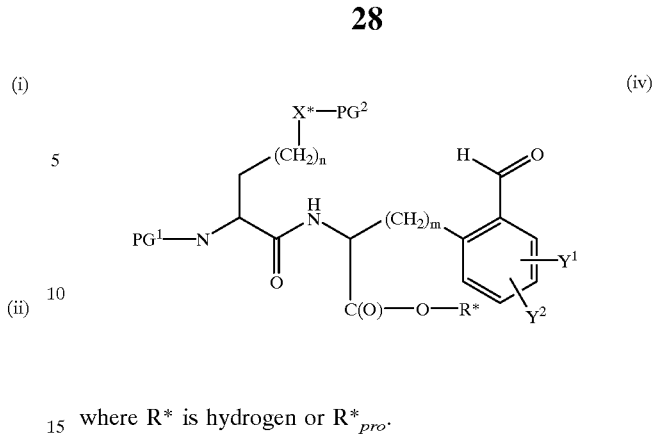

(iv)

where R* is hydrogen or R*$_{pro}$.

5. A compound having the following formula iv, and salts thereof:

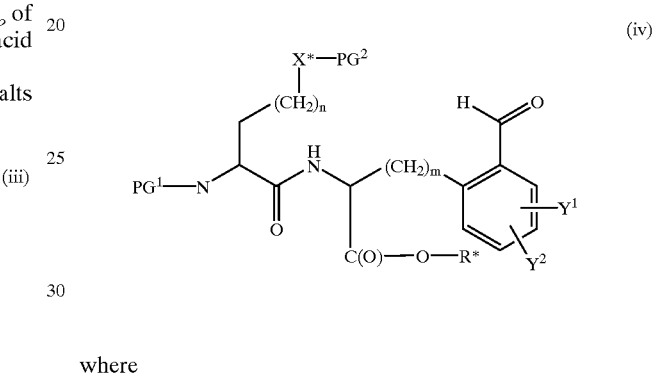

(iv)

where

Y$^1$, and Y$^2$ are each independently hydrogen, alkyl, aryl, halogen, or alkoxy;

R* denotes hydrogen, alkyl, substituted alkyl, aryl-(CH$_2$)$_p$—, substituted aryl-(CH$_2$)$_p$—, heteroaryl-(CH$_2$)$_p$—, or other carboxylic acid protecting group;

X* is O or S;

PG$^1$-N— denotes a protected nitrogen atom;

PG$^2$ denotes a hydroxy or mercapto protecting group;

m is zero or one;

n is zero or one; and p is zero or an integer from 1 to 6.

6. A compound of claim 5, wherein said compound is N-[S-acetyl-N-[(phenylmethoxy)carbonyl]-L-homocysteinyl]-2-formyl-L-phenylalanine, methyl ester having the structure:

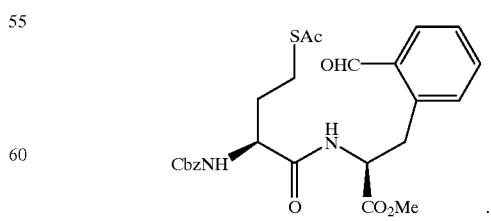

7. The method of claim 4, wherein, further, the group X* of said compound of the formula iv is deprotected to form a compound of the following formula v:

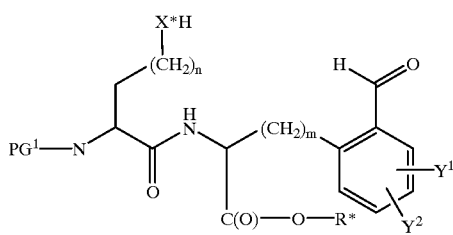

and, optionally, where X* is O, converting X* to S.

8. A compound having the following formula v, and salts thereof:

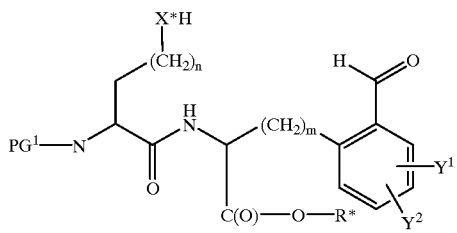

(v)

where (v) Y¹ and Y² are each independently hydrogen, alkyl, aryl, halogen, or alkoxy;

R* denotes hydrogen, alkyl, substituted alkyl, aryl-$(CH_2)_p$—, substituted aryl-$(CH_2)_p$—, heteroaryl-$(CH_2)_p$—, or other carboxylic acid protecting group;

X* is O or S;

$PG^1$-N— denotes a protected nitrogen atom;

m is zero or one;

n is zero or one; and p is zero or an integer from 1 to 6.

9. A compound of claim 8, wherein said compound is 2-formyl-N-[N-[(phenylmethoxy)carbonyl]-L-homocysteinyl]-L-phenylalanine, methyl ester having the structure:

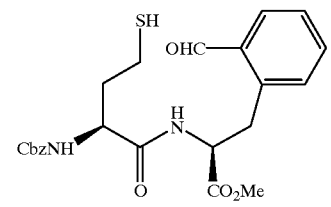

* * * * *